US010086151B2

United States Patent
Clark

(10) Patent No.: US 10,086,151 B2
(45) Date of Patent: Oct. 2, 2018

(54) NEEDLE ASSEMBLY

(71) Applicant: SMITHS MEDICAL ASD, INC., Rockland, MA (US)

(72) Inventor: Geoff Clark, Lempster, NH (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 1068 days.

(21) Appl. No.: 13/827,417

(22) Filed: Mar. 14, 2013

(65) Prior Publication Data

US 2014/0039414 A1 Feb. 6, 2014

Related U.S. Application Data

(63) Continuation-in-part of application No. 13/567,122, filed on Aug. 6, 2012, now Pat. No. 9,861,383.

(51) Int. Cl.
*A61M 5/32* (2006.01)
*A61B 17/34* (2006.01)

(52) U.S. Cl.
CPC ....... *A61M 5/3293* (2013.01); *A61B 17/3401* (2013.01); *A61M 5/3287* (2013.01);
(Continued)

(58) Field of Classification Search
CPC ..... A61B 17/3401; A61B 2017/00455; A61M 25/0606; A61M 2205/586;
(Continued)

(56) References Cited

U.S. PATENT DOCUMENTS 3,506,007 A 4/1970 Henkin
D269,549 S 6/1983 Gross
(Continued)

FOREIGN PATENT DOCUMENTS

EP 0583144 2/1994
EP 0792659 9/1997
(Continued)

OTHER PUBLICATIONS

PCT International Search Report and Written Opinion re PCT/US2012/051652, dated Jan. 21, 2013 by ISA/KR.
(Continued)

*Primary Examiner* — Emily Schmidt
(74) *Attorney, Agent, or Firm* — Louis Woo

(57) ABSTRACT

A needle assembly has a needle hub that has a body to which are formed two plates at opposite sides thereof in a parallel relationship. The plates have respective upper edges and lower edges that lie substantially along respective planes, so that the needle hub may be stably placed onto a surface by means of the respective edges. A partition is formed orthogonally proximate to the front ends of the parallel plates. The partition and the parallel plates together provide upper and lower three point stable supports for the needle hub. A notch at the partition provides a guided line of sight to the tip of the needle for the user. The connector at the proximal portion of the needle hub has a non-conventional configuration that allows it to mate only with a counterpart special connector of a fluid conveying device that has a complementary non-conventional configuration.

20 Claims, 10 Drawing Sheets

(52) U.S. Cl.
CPC ............... *A61M 2205/586* (2013.01); *A61M 2205/6045* (2013.01)

(58) Field of Classification Search
CPC .. A61M 2205/6045; A61M 2005/1587; A61M 19/00
See application file for complete search history.

(56) References Cited

U.S. PATENT DOCUMENTS

| | | | |
|---|---|---|---|
| D282,008 S | 12/1985 | McFarlane | |
| D302,589 S | 8/1989 | McMenamy et al. | |
| 5,211,644 A | 5/1993 | VanBeek et al. | |
| 5,215,528 A | 6/1993 | Purdy | |
| 5,545,152 A | 8/1996 | Funderbuck et al. | |
| 5,571,091 A | 11/1996 | Davis et al. | |
| D378,405 S | 3/1997 | Musgrave et al. | |
| 5,651,776 A | 7/1997 | Appling et al. | |
| D378,130 S | 3/1998 | Schmidt | |
| D397,434 S | 8/1998 | Pike | |
| 5,853,391 A | 12/1998 | Bell | |
| 5,855,230 A | 1/1999 | Guala et al. | |
| D417,733 S | 12/1999 | Howell et al. | |
| D421,119 S | 2/2000 | Musgrave et al. | |
| 6,027,480 A | 2/2000 | Davis et al. | |
| 6,197,007 B1 | 3/2001 | Thorne et al. | |
| D452,003 S | 12/2001 | Niermann | |
| D452,314 S | 12/2001 | Niermann | |
| 6,475,190 B2 | 11/2002 | Young | |
| 6,506,181 B2 | 1/2003 | Meng et al. | |
| D469,870 S | 2/2003 | Niermann et al. | |
| D471,980 S | 3/2003 | Caizza | |
| 6,558,353 B2 | 5/2003 | Zohmann | |
| 6,656,161 B2 | 12/2003 | Young et al. | |
| 6,887,417 B1 | 5/2005 | Gawreluk et al. | |
| 6,953,448 B2 | 10/2005 | Moulton et al. | |
| D523,956 S | 6/2006 | Guala | |
| D607,100 S | 12/2009 | Uchida et al. | |
| 7,658,725 B2 | 2/2010 | Bialecki et al. | |
| D640,785 S | 6/2011 | Lee | |
| 7,955,315 B2 | 6/2011 | Feinberg et al. | |
| D655,406 S | 3/2012 | Ma et al. | |
| D669,577 S | 10/2012 | Holsinger | |
| D679,803 S | 4/2013 | Carter | |
| 2003/0050611 A1 | 3/2003 | Cindrich | |
| 2003/0069542 A1 | 4/2003 | Meng et al. | |
| 2004/0167474 A1 | 8/2004 | Meng et al. | |
| 2005/0090801 A1 | 4/2005 | Racz et al. | |
| 2007/0270758 A1 | 11/2007 | Hanner et al. | |
| 2008/0287919 A1* | 11/2008 | Kimball | 604/533 |
| 2012/0004625 A1 | 1/2012 | Velez-Rivera | |
| 2012/0172805 A1* | 7/2012 | Stevenson | 604/164.01 |
| 2012/0326438 A1* | 12/2012 | Robert et al. | 285/305 |

FOREIGN PATENT DOCUMENTS

| | | |
|---|---|---|
| EP | 2335766 | 6/2011 |
| WO | WO 02/45781 A2 | 6/2002 |
| WO | 2005/044335 | 10/2004 |
| WO | WO 2008/149205 A1 | 12/2008 |
| WO | WO 2008/157376 A1 | 12/2008 |

OTHER PUBLICATIONS

Supplementary European Search Report and Search Opinion, dated Jan. 21, 2015, EP Application No. 12827631.8.

* cited by examiner

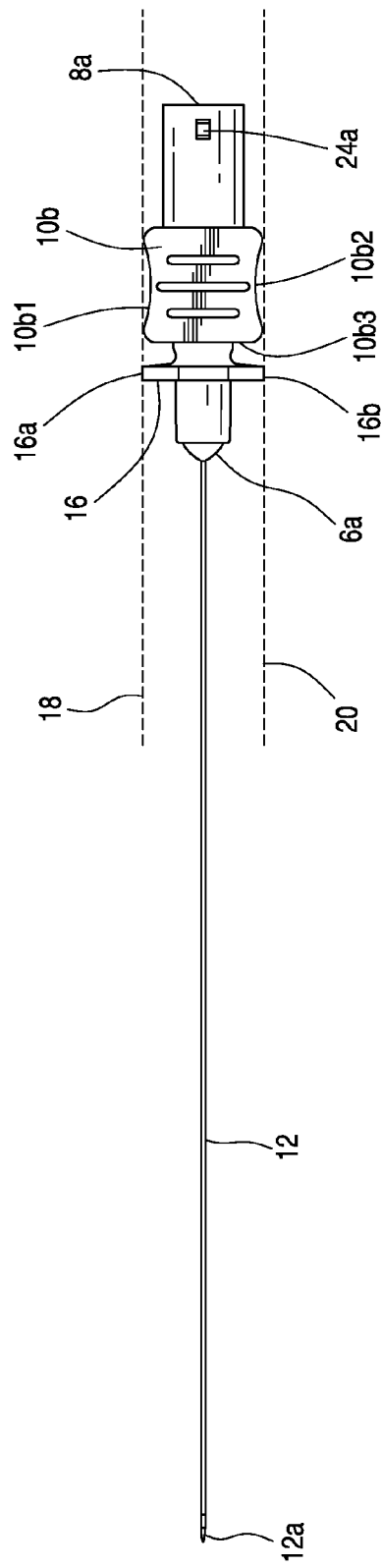
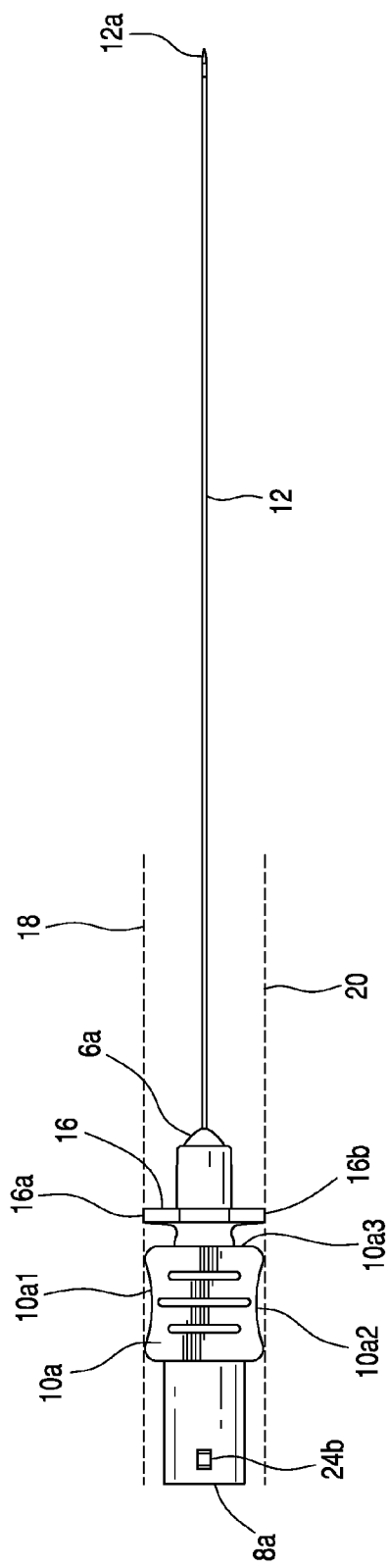
FIG. 3
FIG. 4

NEEDLE ASSEMBLY

CROSS REFERENCES TO RELATED APPLICATIONS

This application is a continuation-in-part application of application Ser. No. 13/567,122 filed on Aug. 6, 2012.

FIELD OF THE INVENTION

The present invention relates to needle assemblies, and particularly to a needle assembly that has a specially designed hub that enables a user to firmly grasp and manipulate the needle for insertion to a patient. The connector end of the hub has a non-conventional configuration that prevents the needle hub from connecting to conventional counterpart connectors.

BACKGROUND OF THE INVENTION

Some of the prior art spinal and epidural needles tend to be somewhat difficult to manipulate by a surgeon or anesthesiologist, when inserting the needle into the patient. The prior art does disclose some needle hubs that have means for the user to grasp. Such prior art includes U.S. Pat. Nos. 6,027,480, D378,405, D421,119 and D469,870. However, those needle hubs do not provide means to prevent the user from inadvertently making contact with the needle or guide the insertion of the needle to the patient, or have a connector that prevents mis-connection. The instant invention needle assembly is an improvement of the prior art needle assembles.

SUMMARY OF THE PRESENT INVENTION

The needle assembly of the instant invention has a needle hub that has a main body having a distal portion with a closed distal end to which a needle extends and a proximal portion to which there is an opened proximal end for connection to a fluid store such as a syringe or a fluid line. The body is a substantially cylindrical body with the distal portion sloping downwards from where it merges with the proximal portion towards the closed distal end. Two substantially rectangular plates are formed on opposite sides of the body that bridges the proximal and distal portions. The plates are bonded to the body in a parallel relationship, with the respective upper edges and the respective lower edges being substantially correspondingly coplanar. Accordingly, as the respective upper edges and respective lower edges of the two plates lie along corresponding planes, the needle hub, when placed onto a flat surface with either the respective upper edges or the respective lower edges, would stay put without rolling.

Proximate or adjacent to the two plates there is a partition at the distal portion of the needle hub body formed orthogonally to the longitudinal axis of the needle, and therefore orthogonal to the two plates that are bonded to opposite sides of the main body. The partition has its top edge in substantial coplanar alignment with the upper edges and its bottom edge in substantial coplanar alignment with respective lower edges of the two plates. As a result, upper and lower three point stable supports are provided by the respective edges of the two plates and the partition at their respective upper edges or their respective lower edges. This configuration ensures that when the needle assembly is put on a flat surface, it will not move due to unintentional rolling. In addition to providing additional support, the partition, being positioned at the distal portion of the needle hub, prevents the fingers of the user from inadvertently coming into contact with the needle that extends from the closed distal end.

There is a notch formed at the partition extending from its upper edge inwardly towards the body of the hub to provide a line of sight that extends to the bevel tip of the needle, which may include an orifice that opens on the side of the needle. The notch at the partition provides a line of sight from the needle tip to the space between the upper portion of the two plates which a user can use as a sight guide to insert the needle into the patient.

The opened proximal end of the needle hub forms the connector that connects the needle assembly to the fluid source. The proximal end is configured to have two protuberances that extend on opposite sides at the proximal portion of the body. In addition, the opening at the proximal end is configured such that the connector of the needle hub is matable only to a counterpart connector that has a complementary configuration. Also formed at the proximal end is a keyway that guides the insertion of a stylet into the needle to prevent the coring of the needle during its insertion into the patient.

BRIEF DESCRIPTION OF THE FIGURES

The present invention will become apparent and the invention itself will be best understood with reference to the following description of the present invention taken in conjunction with the accompanying drawings, wherein:

FIG. 3 is one side view of the inventive needle assembly;

FIG. 4 is another side view of the inventive needle assembly;

DETAILED DESCRIPTION OF THE INVENTION

Figure 1:
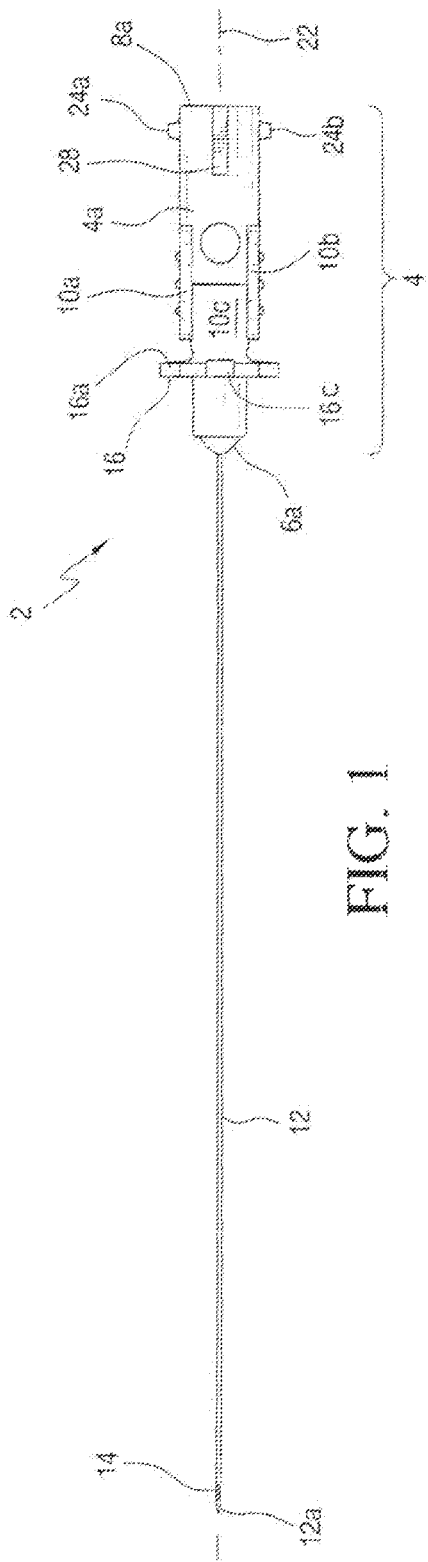
FIG. 1 is a top view of the needle assembly of the instant invention.

With reference to the figures, needle assembly 2 of the instant invention is shown to have a needle hub 4 that includes a distal portion 6 and a proximal portion 8. It should be appreciated that although designated as such in FIG. 2, there is no actual line of demarcation between distal portion 6 and proximal portion 8. Distal portion 6 has a closed distal end 6a, whereas proximal portion 8 has an opened proximal end 8a. Needle hub 4 has a main body 4a that is substantially cylindrical along proximal portion 8 and slopes or inclines downwards in a conical fashion towards distal end 6a along distal portion 6.

Figure 2:
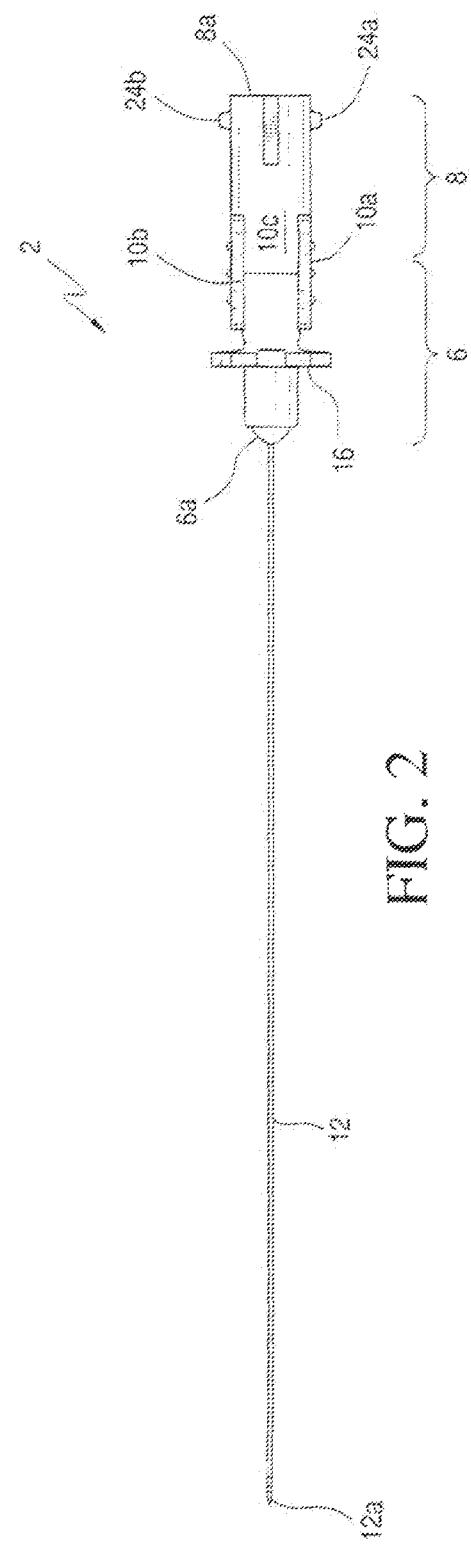
FIG. 2 is the bottom view of the inventive needle assembly.
Figure 5:
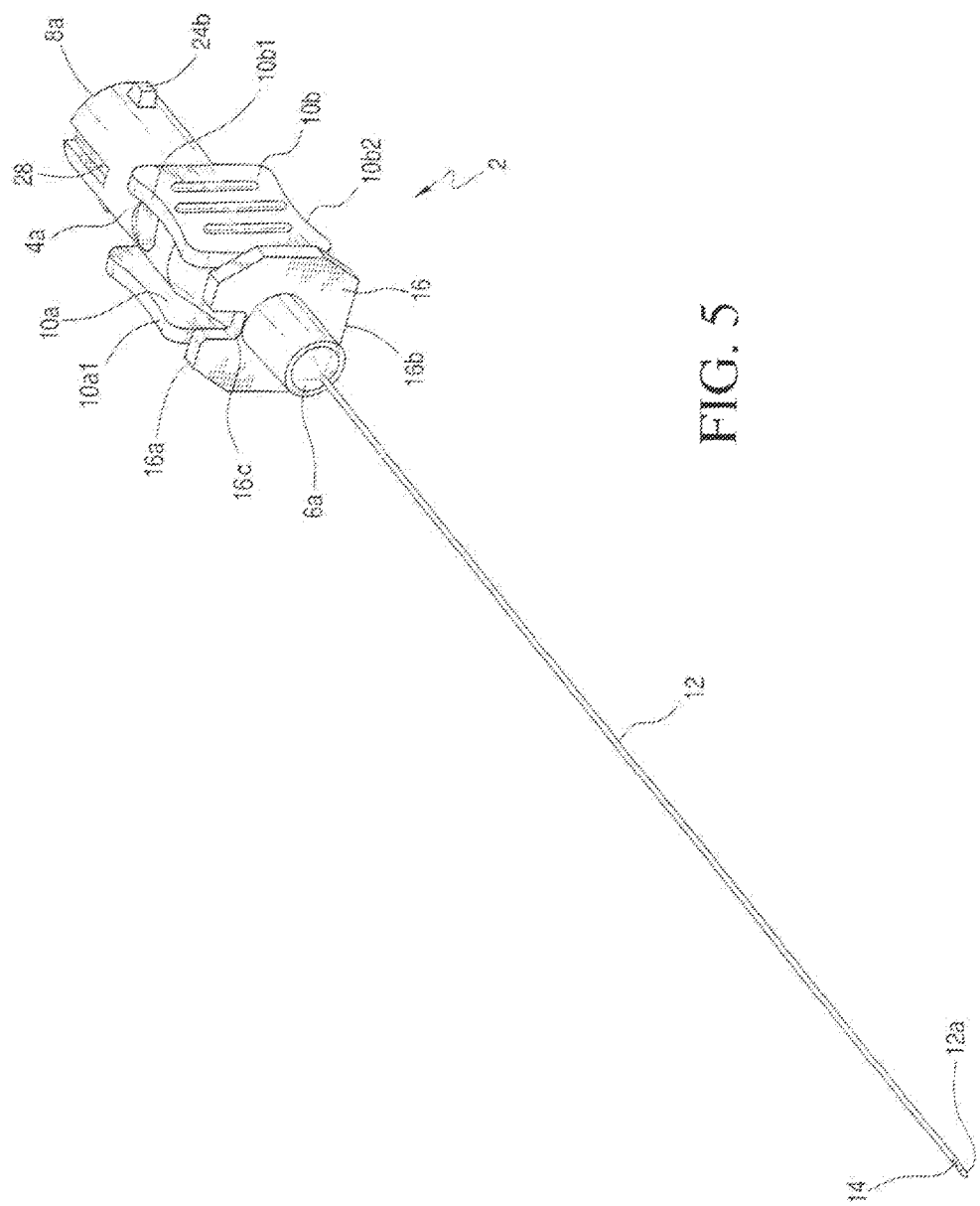
FIG. 5 is a perspective front view of the inventive needle assembly.

Two flats or plates 10a and 10b are bonded to body 4a bridging distal portion 6 and proximal portion 8. Plates 10a and 10b each are substantially rectangular in shape, with their respective upper edges 10a1, 10b1 and their respective lower edges 10a2 and 10b2, slightly curved inwardly to form a slight concave configuration. For the instant invention, the respective upper edges 10a1 and 10b1 of plates 10a and 10b are deemed to lie substantially co-planarly along an upper plane, designated by dotted line 18 in FIG. 3; and the respective lower edges 10a2 and 10b2 of plates 10a and 10b are deemed to lie substantially co-planarly along a lower plane, designated by dotted line 20 in FIG. 3. Thus, the respective upper edges form one rest support for the needle hub, if the needle hub were to be placed on a flat surface using the respective upper edges 10a1 and 10b1. Likewise, the respective lower edges 10a2 and 10b2 form another rest support whereby the needle can be placed onto a flat surface by using those edges. Once placed onto a flat surface, the respective upper and lower edges each provide support for the needle hub, and prevent the needle hub from rolling. As best shown in FIGS. 1 and 2, plates 10a and 10b are formed in parallel to each other in a relationship that defines a space 10c between the two plates.

At the closed distal end 6a there is extending from needle hub 4 a needle 12. For the embodiment shown in the figures, needle 12 may be a spinal or epidural needle that has a closed end 12a and a side opening or orifice 14 proximate to the closed end 12a where through fluid from the needle may traverse. Although a needle with a closed end and a side orifice is shown, it should be appreciated that a spinal or epidural needle having an opened end tip is equally applicable for the instant invention.

At distal portion 6 between the respective front edges 10a3 and 10b3 of plates 10a and 10b and distal end 6a there is integrally formed at needle hub 4 a partition plate, or simply a partition 16, orthogonally to the longitudinal axis 22 of the needle assembly. Partition 16 therefore is orthogonal to plates 10a and 10b, and provides a stop for the fingers (defined to include the thumb) of a clinician user, if the user is grasping plates 10a and 10b with his fingers, for example with his thumb and fore finger. As partition 16 prevents the fingers of the user from inadvertently making contact with needle 12, plates 10a and 10b prevent the needle from rolling between the fingers of the clinician user to ensure that the orientation of the tip of the needle may continuously be monitored by the user.

Partition 16 is substantially rectangular and has an upper edge 16a and a lower edge 16b. As best shown in FIG. 3, upper edge 16a of plate 16 lies in a coplanar relationship with edges 10b1 and 10a1 of plates 10b and 10a, respectively, along plane 18. Similarly, the lower edge 16b of partition 16 lies co-planarly with respective lower edges 10a2 and 10b2 of plates 10a and 10b along plane 20. See FIGS. 3 and 4. As a result, top edge 16a of partition 16 and top edges 10a1 and 10b1 of plates 10a and 10b together form a multiple point stable support for the needle hub 4, were the needle hub to be rested on a flat surface by means of those edges. Likewise, bottom edge 16b of partition 16 and respective bottom edges 10a2 and 10b2 of plates 10a and 10b together provide a multiple point stable support to ensure that the needle hub would not move once it has been placed onto a flat surface supported by those lower edges.

Partition 16 has a notch 16c that extends from its top edge 16a inwardly towards the longitudinal axis 22. Notch 16c is formed such that it provides a line of sight from needle tip 12a to space 10c defined between plates 10a and 10b at the top portion of the needle hub. Notch 16c may act as a sight guide for the user to ensure that the bevel end of the needle, and/or also the side orifice 14, be correctly inserted into the patient. By grasping plates 10a and 10b with his thumb and fore finger and biasing the front portions of those digits against the side of partition 16 that faces plates 10a and 10b, the user can readily manipulate the needle since the rolling of the needle between the fingers of the user is prevented as discussed above. And by using partition 16 as a push plate, with the aid of notch 16c, the orientation of the tip of the needle is continuously monitored as the user guidedly inserts the needle into the patient, so as to ensure the correct placement of the tip of the needle in the patient.

The connector of needle hub 4 is provided at the end of proximal portion 8 close to the opened proximal end 8a. As shown, two protuberances 24a and 24b are provided at opposite sides of the connector at proximal portion 8. The protuberances are configured such that they are engagable only with a counterpart connector that has complementary channels or grooves for accepting them. Also, the opening 26 (FIG. 6) at proximal end 8a has a dimension that allows the connector to only mate with a counterpart non-conventional connector that has a complementary dimensioned opening, so that needle hub 4 will not connect to a counterpart connector that has a conventional luer connector defined by International Standard Organization (ISO) standards. The dimension(s) of an exemplar non-conventional connecter that may be used for the connector portion of the needle assembly of the instant invention may be gleaned from co-pending application 61/457,879 filed on Jun. 27, 2011. The disclosure of the '879 application is incorporated by reference to the disclosure of the instant application.

Figure 7:
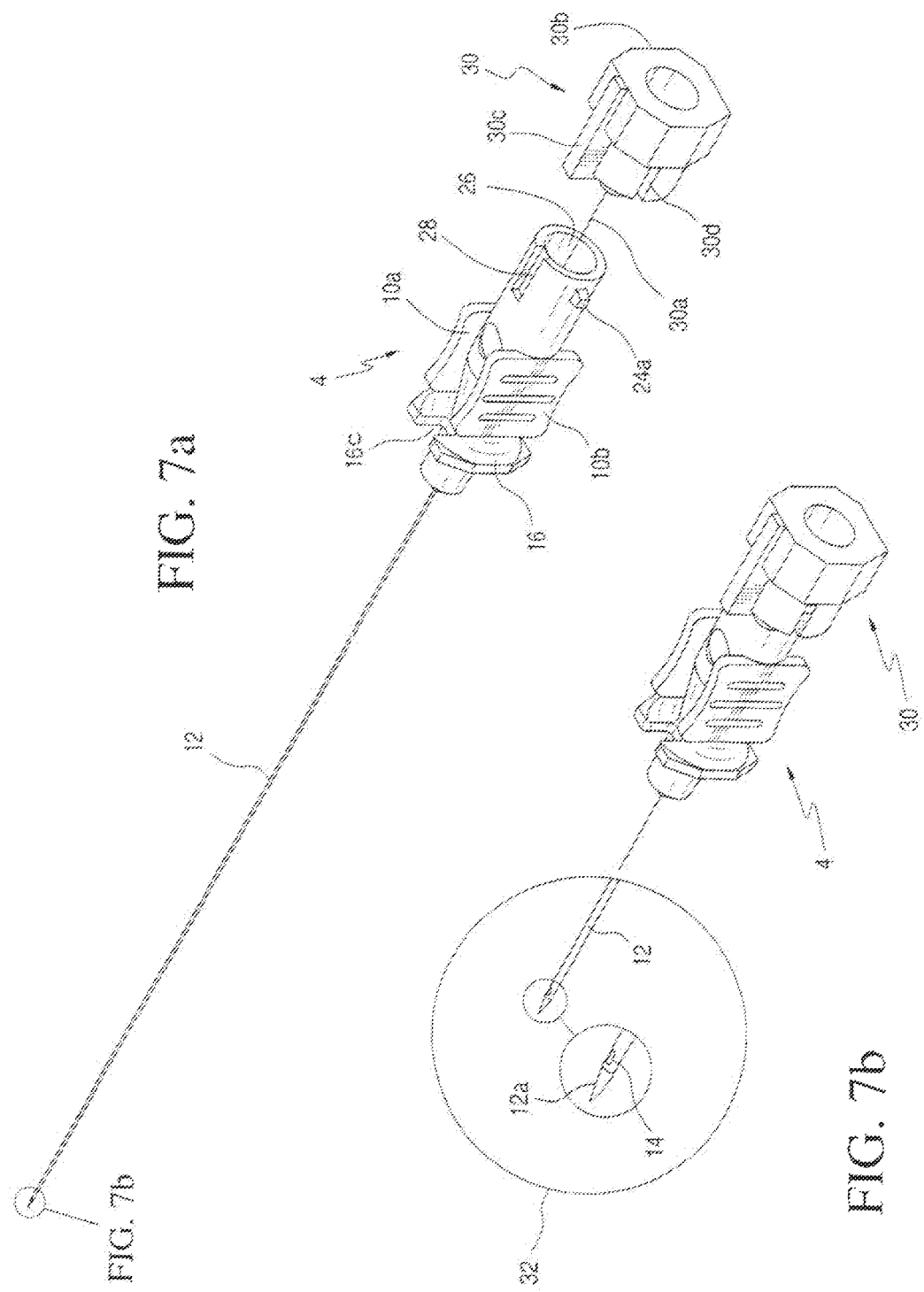
FIG. 7a is a perspective view of the needle assembly of the instant invention having the needle of a stylet partially inserted thereinto.
FIG. 7b is another perspective view of the needle assembly of the instant invention having inserted therein the needle of the stylet.

A keyway 28 that extends from proximal end 8a inwardly to body 4a along the longitudinal axis 22 provides a guide, at proximal portion 8, for accepting a stylet 30 (FIGS. 7a and 7b) that includes a stylet needle 30a and its hub 30b. As shown, stylet hub 30b has a finger 30c that slidably fits into keyway 28, when stylet hub 30b is fitted to the connector portion of needle hub 4. There are also slots 30d, only one being shown, that allow stylet hub 30b to fit onto proximal portion 8 without interference from protuberances 24a and 24b. With stylet 30 fully inserted into hub 4, per shown in FIG. 7b, side orifice 14 of needle 12, per shown in the exploded view 32 of FIG. 7b, is blocked by stylet needle 30a, so that there would not be any coring by needle 12, when needle 12 is inserted into the patient. Once the needle is properly placed within the patient, stylet 30 is removed, so that medicament may be conveyed to the patient by means of side orifice 14 of needle 12. In the case of an open ended spinal needle, the stylet blocks the opened end of the needle while it is inserted in the needle. It should be appreciate that even though a spinal needle is shown by the figures, an epidural needle (which has an opened end tip) may also be fitted with the inventive needle hub disclosed herein.

Figure 8:
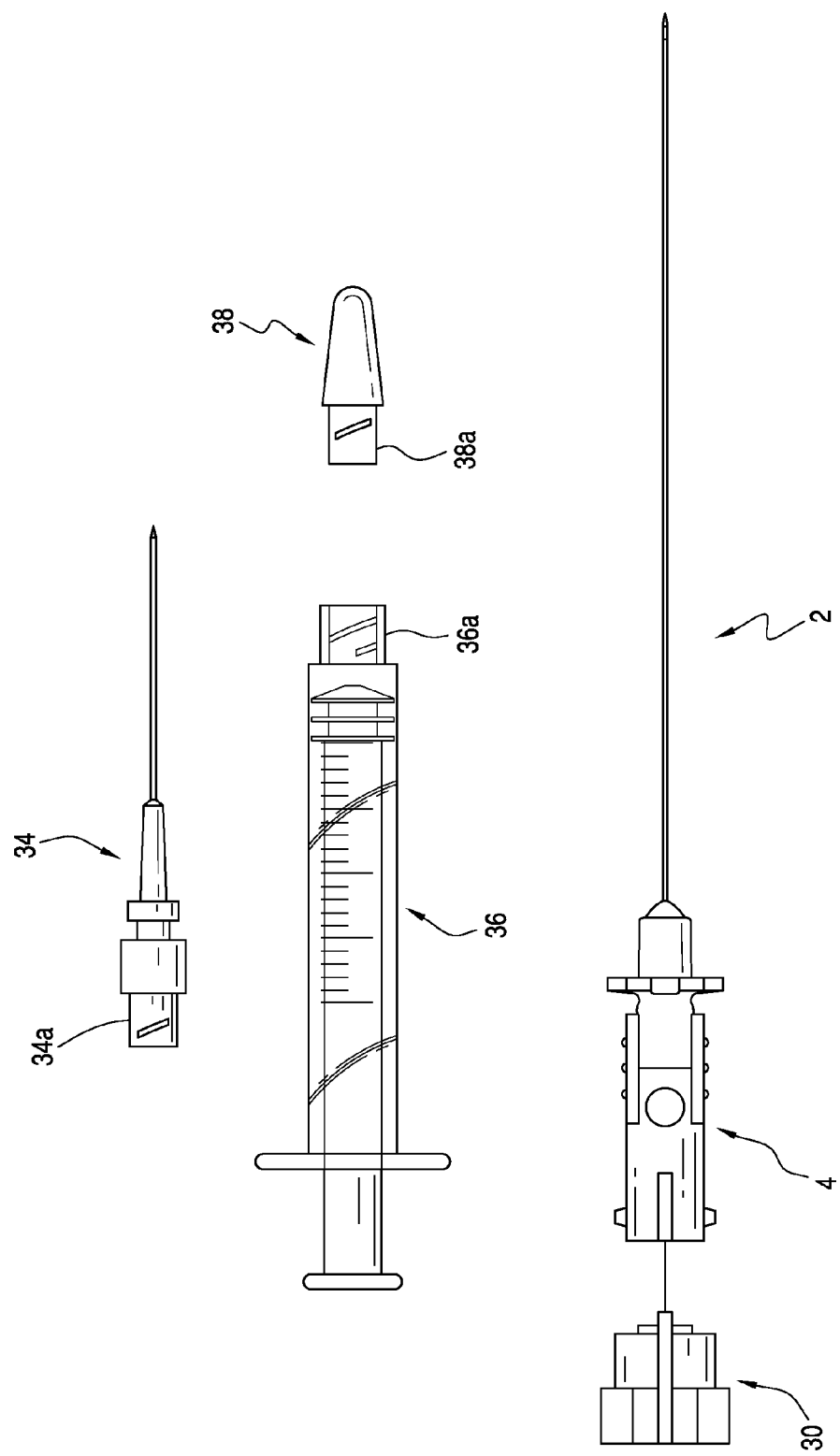
FIG. 8 is an illustration of the needle assembly of the instant invention, and other components that may be used in conjunction therewith.

FIG. 8 shows the various components that may be used with the needle assembly 2 of the instant invention. As shown, there is a syringe 36 provided with a receptacle end 36a having a configuration complementary to the connector portion of needle hub 4. A cap 38 that has a connector portion 38a having a configuration similar to the connecter portion of needle hub 4 is provided to cap the receptacle end 36a of syringe 36, prior to its use, so as to prevent possible contamination thereof. Syringe 36 may be used with a filter needle 34 that has a connector portion 34a dimensionally configured to be connectable to receptacle end 36a of syringe 36.

In use, cap 38 is removed from syringe 36. Needle 34 is then connected to syringe 36 so that medicament may be withdrawn from a vial (not shown) via needle 34 into syringe 36. Thereafter, needle 34 is discarded. Prior to or after the medicament has been withdrawn from the vial into syringe 36, the surgeon or anesthesiologist would insert the needle 12 of needle assembly 2 into the patient, for example spinally or epidurally. Once the needle 12 is correctly positioned in the patient, and after syringe 36 is filled with the appropriate medicament, needle hub 4 and syringe 36 are matingly coupled together so that the medicament stored in the syringe may be conveyed into the patient, in a manner well known in the art for example by pushing the plunger of the syringe. Although FIG. 8 illustrates one exemplar embodiment procedure for utilizing the needle assembly, it should be appreciated that the needle assembly of the instant invention may be an epidural needle having a connector for connection with a syringe for injection, or an epidural needle utilized to place an epidural catheter into the patient, with the epidural catheter connected to a fluid store such as a fluid line or a fluid cassette after the removal of the epidural needle as is well known in the art. The medicament may then be dispensed through the catheter to the patient by a syringe or an infusion pump.

Figure 6:
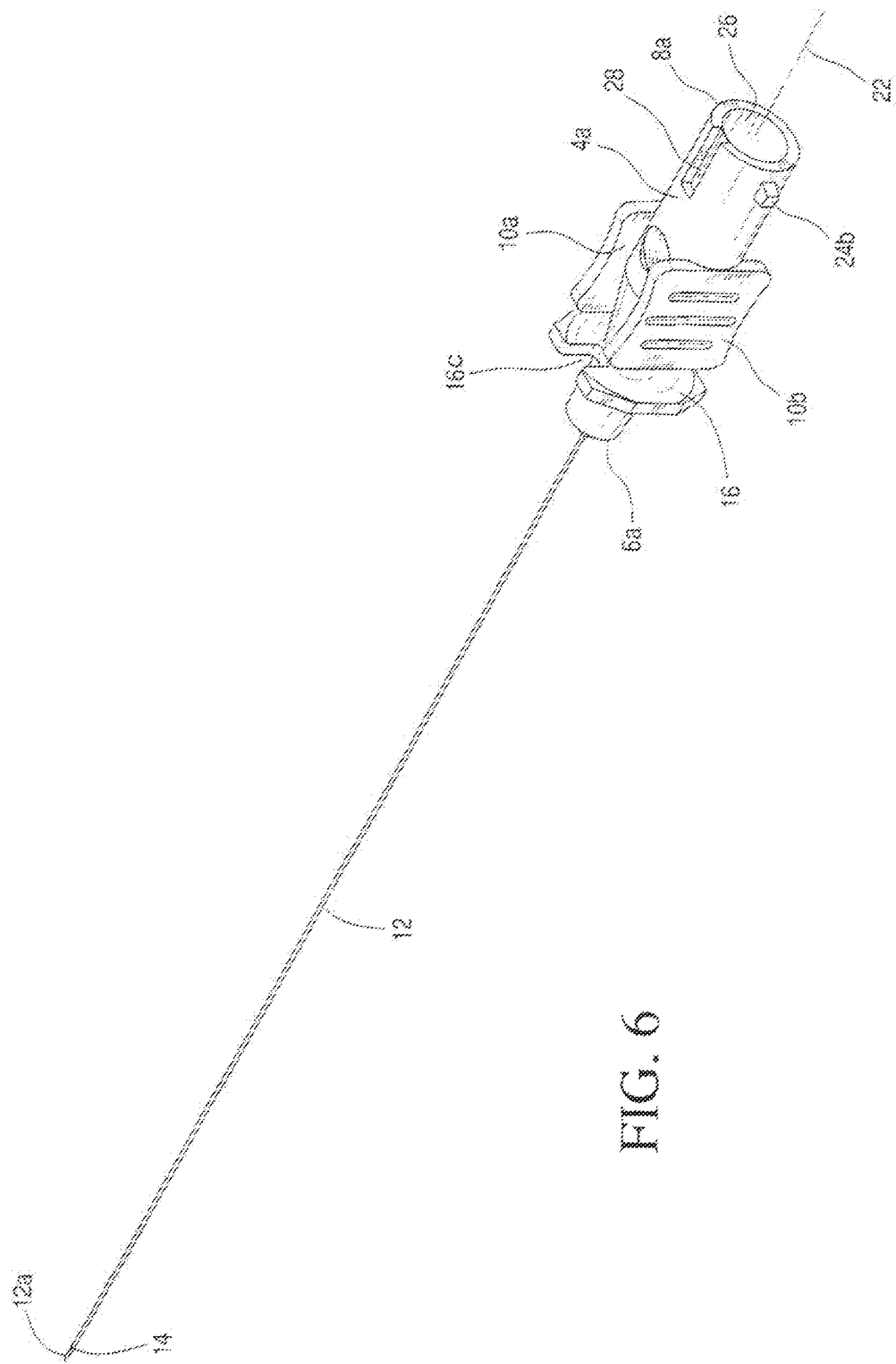
FIG. 6 is a perspective rear view of the inventive needle assembly.

With reference to FIG. 6 and the relevant disclosure form the above-noted incorporated by reference application No. 61/457,879, now application Ser. No. 13/517,782 filed on Jun. 14, 2012, the exemplar needle hub 4 has a female connector at its proximal end 8 that has a given or particular dimension(s), feature(s) and/or configuration that allows it to be connected to a counterpart connector such as the male connector 36a of syringe 36 (FIG. 8) that has a complementary dimension(s), feature(s) and/or configuration to the proximal portion 8 of needle hub 4 of the needle assembly 2. Connector 36a is an integral extension of syringe 36. Thus, male connector 36a, which includes a nose cone extension to be discussed further with reference to FIG. 10, and the female connector at needle hub 4 have complementary features, dimensions and/or configurations that allow those connectors to matingly coupled, connected or fitted to each other, but not with standard connectors such as luer connectors that have conventional configurations manufactured in accordance with ISO (International Standard Organization) Standards 591-1 and 594-2. For ease of discussion, henceforth it should be assumed that the term "configuration" is inclusive of the dimensions and other features of the being discussed connectors that either enable or prevent those connectors and their counterparts (male and female) from matingly connect or couple to each other.

Figure 9:
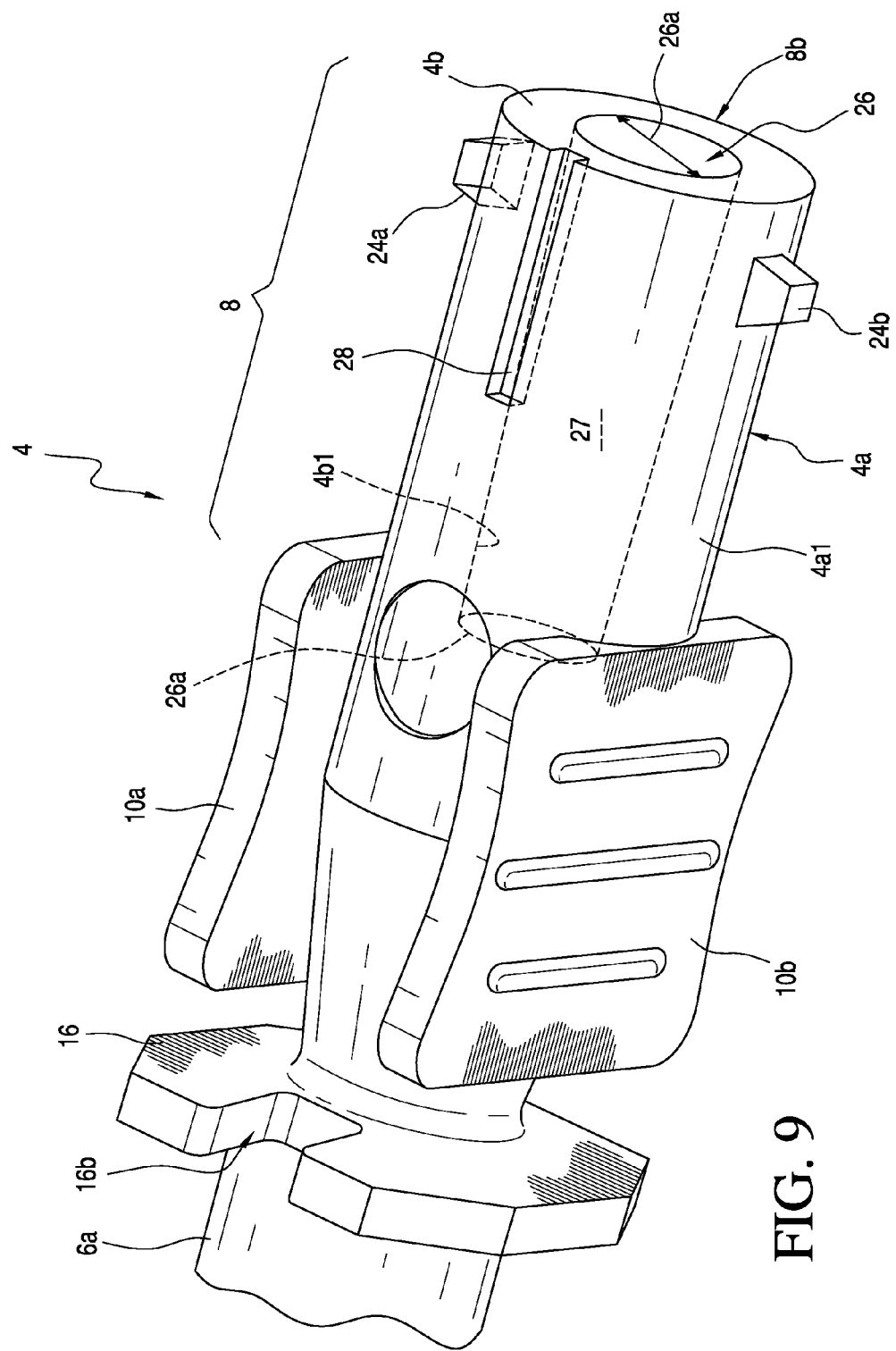
FIG. 9 is another view of the needle hub shown in FIG. 4 amplified to illustrate the special non-conventional configuration at its connector end.

The needle hub 4 shown in FIG. 6 is reproduced in a semi-see-through view of FIG. 9. As shown, the proximal portion 8 of needle hub 4 has an elongate substantially cylindrical body, represented by main body 4a that has an opening 26 at its proximal end 8b. The elongate body 4a has two bosses or protrusions 24a and 24b extending from opposite sides of its outer surface 4a1. Opening 26 forms the mouth of a through bore 27 that extends into body 4a. Although not shown, as is well known, bore 27, possibly reduced in diameter, extends throughout the rest of the needle hub 4 to meet with the cannula of needle 4 so that a through passage extends from opening 26 to the close end 6a at the distal end of the distal portion 6 of hub 4, and from there establishing a passageway with needle 12 (FIGS. 1 and 2) that extends to the tip of the needle.

Further with reference to FIG. 9, through bore 27 is shown to be tapered and defined by a circumferential wall 4b whose inner circumferential surface 4b1 forms a cross-sectional dimension that has a decreasing conical cross-section from opening 26 to the distal opening 26a proximately at the end of proximal portion 8. The exemplar dimensions for the non-conventional configuration at the proximal portion 8 of needle hub 4 may be referenced with respect to the above noted application Ser. No. 13/517,782, and will be discussed in greater detail relative to the special connector or connector fitting of a fluid conveying device, for example syringe 36 shown in FIG. 8, that has a counterpart complementary configuration to the non-conventional configuration of needle hub 4. The connector fitting of needle hub 4 shown in FIG. 9 may be referred to as a lock type connector due to protrusions 24a and 24b extending from its outer circumferential surface.

Figure 10:
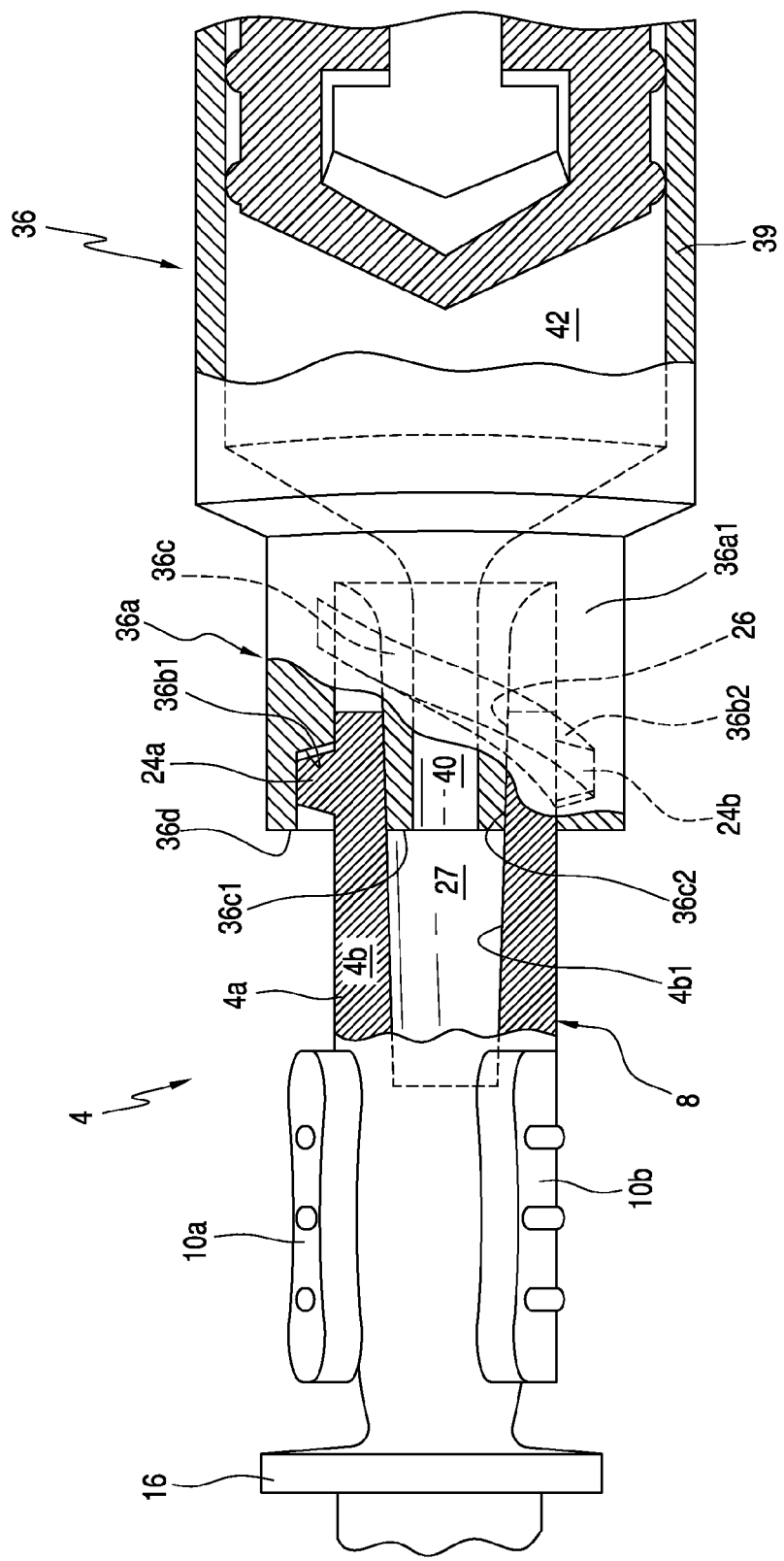
FIG. 10 is a semi-cross sectional view of the inventive needle assembly having a connector of a non-conventional configuration lockingly coupled to a syringe having a special counterpart connector.

With reference to FIG. 10, the exemplar syringe 36 illustrated in FIG. 8 is shown to be lockingly coupled to the lock type needle hub 4 shown in FIG. 9. In particular, syringe 36 has a connector fitting 36a that is a special connector having a counterpart configuration that is complementary to the non-conventional configuration at proximal portion 8 of needle hub 4. As shown, special connector 36a includes a circumferential wall 36a1 that integrally extends from the body 39 of syringe 36. Also extending from the distal end of body 36 is a tapered nose cone or nose cone extension 36c having a through bore 40 that extends from its distal end 36d into chamber 42 of syringe 36. Nose cone extension 36d is surrounded or circumscribed by wall 36a1, which has two spiral grooves 36b1 and 36b2 at its inner surface with corresponding openings at distal end 36d formed to accept protrusions 24a and 24b, respectively, of hub 4. When syringe 36 is coupled to needle hub 4, a through passage is established between chamber 42 and bore 27 of hub 4 via bore 40.

The nose 36c1 of nose cone extension 36c is configured to have a cross-section that is slightly smaller than cross-section 26a of opening 26 of hub 4, so that nose cone extension 36c is readily insertable through opening 26. Moreover, the outer wall 36c2 of tapered nose cone extension 36c is configured to have an increasing conical cross-section from nose 36c1 that complements with the decreasing conical configuration of counter-tapered bore 27 of needle hub 4, so that nose cone extension 36c can fittingly insert into bore 27 of hub 4 to prevent fluid leak from bore 27. Furthermore, with protrusions 24a and 24b of hub 4 threadingly mated to their corresponding grooves 36b1 and 36b2, needle hub 4 and special connector 36a of syringe 36 are lockingly coupled to each other. As was discussed above, given that needle hub 4 has a non-conventional configuration and special connector 36c of syringe 36 has a configuration that is complementary to the non-conventional configuration of needle hub 4, the respective connectors of needle hub 4 and syringe 36 each are not connectable to counterpart conventional connector fittings.

Figure 11:
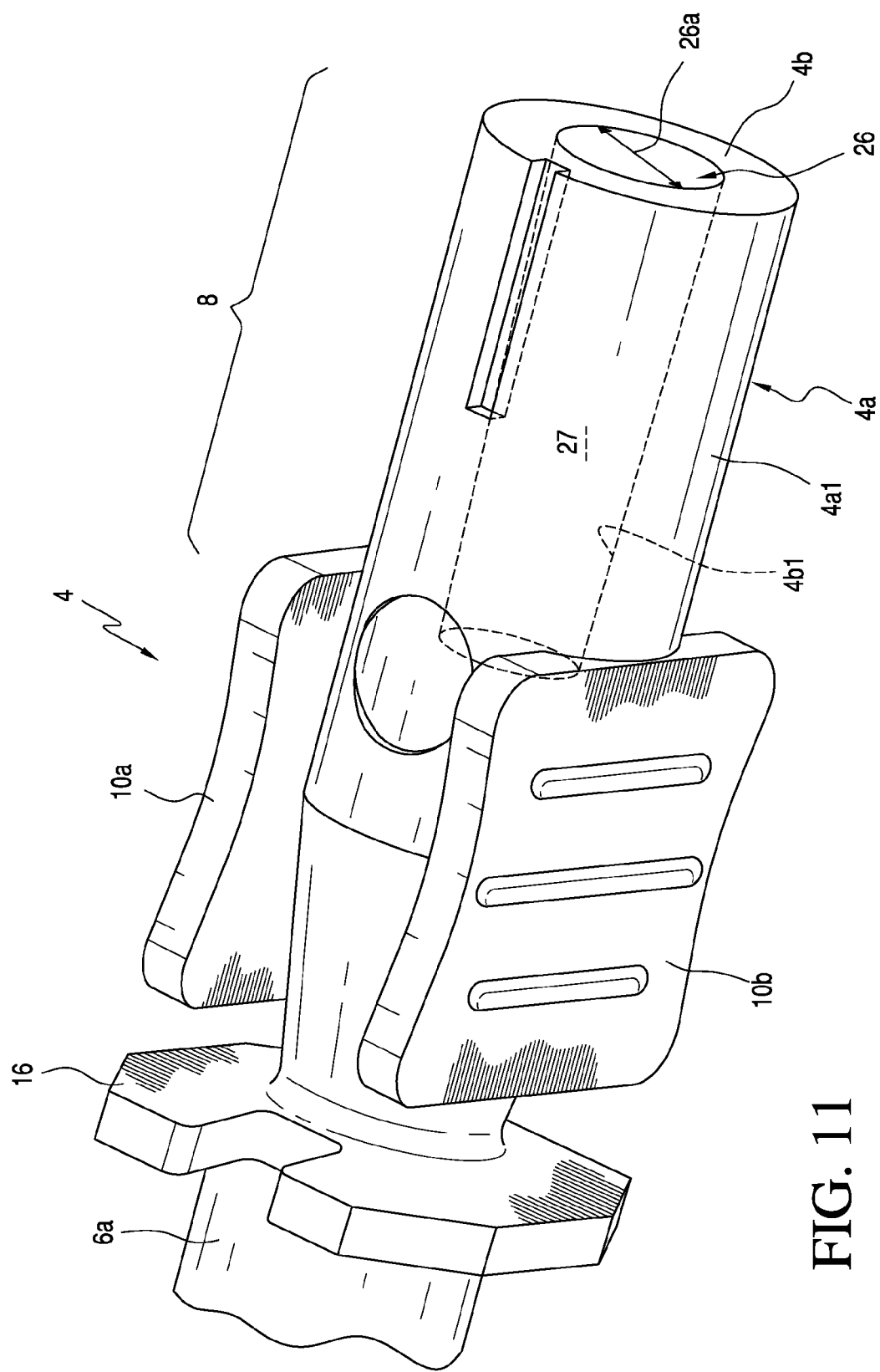
FIG. 11 shows in perspective view a slip fit type needle hub of the needle assembly of the instant invention that has a non-conventional configuration.

FIG. 11 shows a slip fit type connector of the instant invention that has a non-conventional configuration. The non-conventional configuration slip fit connector 4 may have the same components and dimensions as the lock type connector shown in FIG. 9 but without the bosses or protrusions 24a and 24b. Thus, the needle hub 4 of FIG. 11 is fittingly matable to syringe 36 solely by the mating of nose cone extension 36c into bore 27 at the proximal portion 8 of hub 4. Same as the lock type connector discussed above, the outer circumferential wall 36c2 of nose cone extension 36c and the inner circumferential wall 4b1 of the proximal portion 8 that defines bore 27 are configured to have complementary conical increasing/decreasing (or tapered/counter-tapered) configurations that enable nose cone extension 36c to form fittingly slide fit into bore 27 and be frictionally held thereat to establish a fluid tight connection, so that medicament fluid may be conveyed from syringe 36 to the needle extending from needle hub 4.

Figure 12:
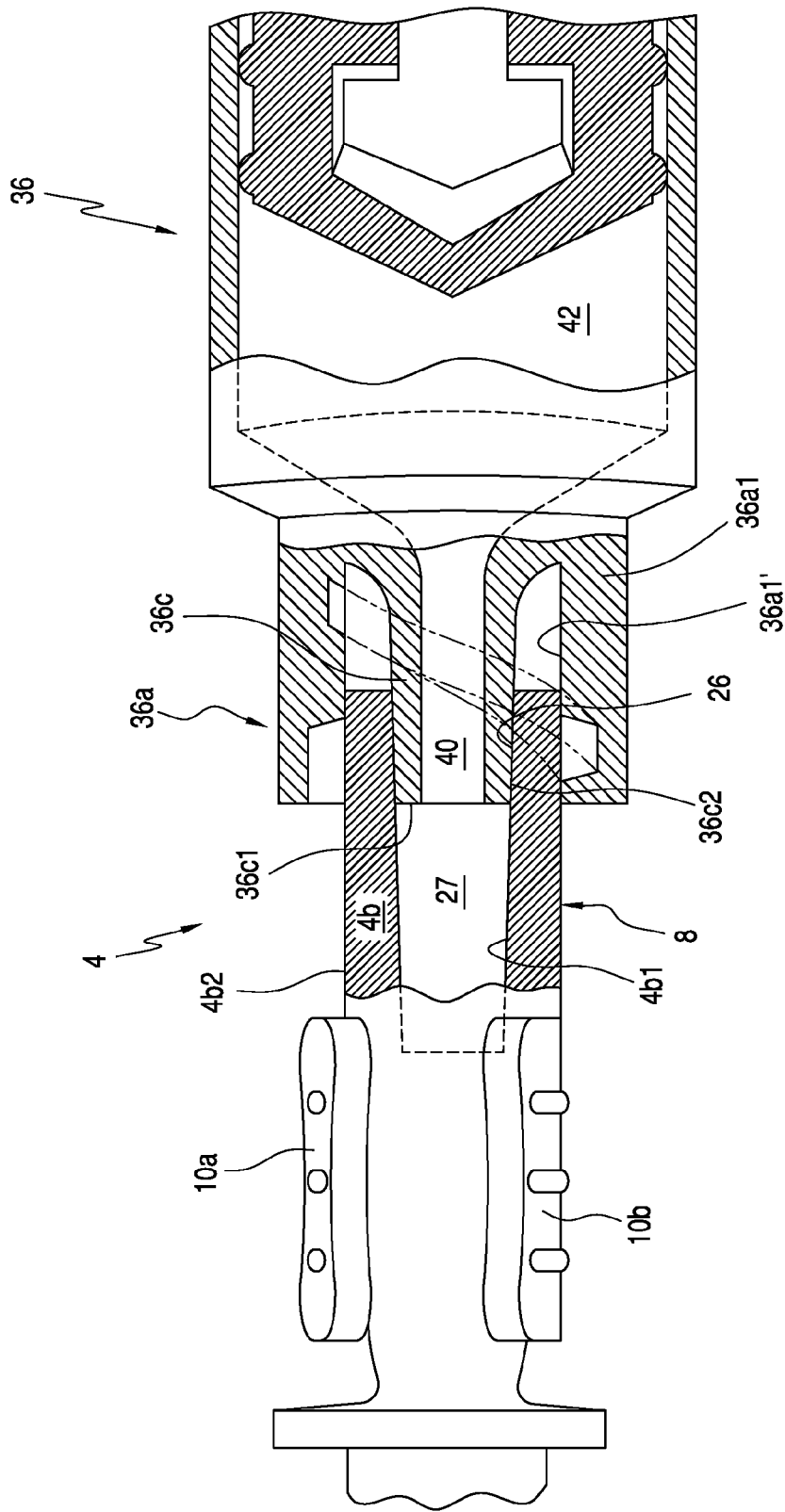
FIG. 12 is a perspective semi-cross sectional view of the needle hub of FIG. 10 fittingly mated to a special counterpart nose cone connector of a syringe.

Note that although circumferential wall 36a1 that circumscribes nose cone extension 36c is shown in FIG. 12, in practice, a circumferential wall is not needed for a slip fit type syringe. Furthermore, as shown in FIG. 12, the slip type connector fitting of hub 4 may also be used with a lock type syringe insofar as proximal portion 8 of the connector has a cross-sectional dimension that is slightly smaller than the cross-sectional dimension of the inner circumferential wall 36a1' of the outer wall 36a1. Thus, per shown in FIG. 12, the inner circumferential wall 4b1 of the needle hub connector and the outer circumferential wall 36c2 of the nose cone extension 36c may be frictionally mated to each other, while the outside circumferential wall 4b2 at the proximal portion 8 of the needle hub and the inner circumferential wall 36a1' of the circumferential wall 36a1 of connector 36a are not in contact with each other, when the slip fit type connector of FIG. 11 is mated to a locked type syringe 36.

Exemplar dimensions of the inventive connectors may be as follows. Opening 26 of the inventive connector 4, shown for example to be female in FIG. 9, has been configured with a taper from approximately 4% to 6%, preferably approximately 5% or 3° (3 degrees), as compared to a taper of 6% or 3.44° for the conventional luer female connectors manufactured under the afore-noted ISO standards. As a result, a conventional male luer connector produced in accordance with the afore-noted ISO standards that otherwise mates readily with a conventional female luer connector could not mate with the inventive female connector, as the configuration of the conventional male luer connector is not complementary to the configuration of the inventive female connector. This is due to the opening 26 and the bore 27 tapering therefrom being configured not to accept the fitting of a conventional luer male connector. There may be other configurations, for example the cross-sectional dimension or the width 26a of the mouth of opening 26, or the thickness of the wall 4b of the connector that would prevent the inventive female connector of hub 4 from mating with a counterpart male luer connector of a conventional configuration.

With reference to FIGS. 10 and 12, the exemplar special male connector 36c is shown to have a nose cone extension or nose portion 36c that has a taper from approximately 4% to 6%, preferably 5% or 3° outwards complement to that of the approximately 5% or 3° inward taper of the counter exemplar bore 27 of the female connector of hub 4 discussed above. Also, the outer circumferential wall 36c2 of nose cone extension 36c has a width that is slightly smaller than the width for the inner circumferential surface 4b1 of the mating portion 4a of the female connector 4, so that nose cone extension 36c can readily fit into the bore 27 of the female connector. The respective widths of the circumferential wall of cone extension 36c and the inner circumferential surface of mating portion 4a of female connector 4 of the instant invention may be dimensioned to be different from (preferably smaller than but could be greater than) those widths or cross sections of the conventional luer connectors noted above so as to act as another feature that prevents the inventive non-conventional configuration connectors from mating to counterpart connectors of conventional configurations.

In as much as the present invention is subject to many variations, modifications and changes in detail, it is intended that the matter described throughout this specification and shown in the accompanying drawings be interpreted as illustrative only and not in a limiting sense. Accordingly, it is intended that the invention be limited only by the spirit and scope of the hereto appended claims.

The invention claimed is:

1. A needle assembly, comprising:
   a hub extending along a longitudinal axis having an open proximal end and a closed distal end;
   a needle having a distal tip and an aperture at or proximate to the tip, the needle having a proximal end connected to the closed end of the hub to establish a through passage between the aperture of the needle and the open end of the hub;
   wherein the hub includes a proximal portion including the proximal end, the proximal portion having a non-conventional configuration that prevents it from coupling with a counterpart conventional connector having a conventional configuration but enables it to mate with a special connector having a counterpart configuration complementary to the non-conventional configuration; and
   wherein the hub further includes a distal portion having two plates positioned at opposite sides thereat in parallel to each other and a partition positioned orthogonal to and separating the two plates from the needle, the respective top edges of the two plates lying substantially co-planarly along an upper plane and the respective bottom edges of the two plates lying substantially co-planarly along a lower plane so that the respective top edges form one rest support and the respective bottom edges form another rest support for the needle hub were the needle hub placed onto a flat surface using the respective top edges or the respective lower edges.

2. Needle assembly of claim 1, wherein the proximal portion of the hub comprises a substantially cylindrical body having an opening at the proximal end to a bore through the cylindrical body, the cross sectional dimension of at least the opening at the proximal end preventing fitting insertion of a nose cone extension of a conventional slip fit connector into the bore.

3. Needle assembly of claim 1, wherein the proximal portion of the hub comprises a substantially cylindrical body having an outer surface and at least one protrusion extending from the outer surface at or proximate to the proximal end, the protrusion preventing a conventional lock connector from mating with the hub.

4. Needle assembly of claim 1, wherein the proximal portion of the hub comprises a substantially cylindrical body having an outer surface and an opening at the proximal end, at least one protrusion extending from the outer surface at or proximate to the proximal end opening, the cross sectional dimension of at least the opening and the protrusion forming the non-conventional configuration.

5. Needle assembly of claim 1, wherein the proximal portion of the hub comprises a substantially cylindrical body having an outer surface and two protrusions extending from opposite sides of the outer surface at or proximate to the proximal end, the protrusions preventing a conventional slip fit or lock connector from mating with the hub.

6. Needle assembly of claim 1, wherein the proximal portion comprises a substantially cylindrical body having an outer surface and an opening of a predetermined cross sectional dimension, two protrusions extending from opposite sides of the outer surface of the cylindrical body at or proximate to the proximal end to form the non-conventional configuration that enables the hub to mate only with a fluid conveying device having the special connector with the counterpart configuration complementary to the non-conventional configuration, the special connector having threads to matingly accept the protrusions and a nose cone extension that fittingly mates with the opening to lockingly couple the needle assembly and the fluid conveying device to each other.

7. Needle assembly of claim 1, wherein the proximal portion comprises a substantially cylindrical body having an outer surface and an opening at the proximal end that opens to a through bore in the cylindrical body, wherein the cylindrical body, the opening and the bore have respective cross sectional dimensions that form the non-conventional configuration that prevents the needle hub from fittingly mating with a conventional slip fit connector.

8. Needle assembly of claim 1, wherein the needle comprises an epidural needle.

9. In combination,
a needle assembly comprising a hub extending along a longitudinal axis having a proximal portion including an open proximal end and a distal portion including a closed distal end, a needle extending from the closed distal end, two plates positioned at opposite sides of the distal end in parallel to each other, the respective top edges of the two plates lying substantially co-planarly along an upper plane and the respective bottom edges of the two plates lying substantially co-planarly along a lower plane so that the respective top edges form one rest support and the respective bottom edges form another rest support for the needle hub were the needle hub placed onto a flat surface using the respective top edges or the respective lower edges, a partition positioned at the distal portion orthogonal to and separating the two plates from the needle, the proximal portion having a non-conventional configuration that prevents it from coupling with a counterpart conventional connector having a conventional configuration but enables it to mate with a special connector having a counterpart configuration complementary to the non-conventional configuration; and
a fluid conveying device having the special connector with the counterpart configuration that is complementary to the non-conventional configuration at the proximal portion of the needle assembly so that the needle assembly and the fluid conveying device are readily matable to each other;
wherein the proximal portion of the needle assembly and the special connector of the fluid conveying device each are not connectable with respective counterpart conventional connectors.

10. Combination of claim 9, wherein the proximal portion of the hub comprises a substantially cylindrical body having an outer surface and an opening at the proximal end to a bore through the cylindrical body, the cross sectional dimension of at least the opening at the proximal end preventing fitting insertion of a nose cone extension of a conventional slip fit connector into the bore.

11. Combination of claim 9, wherein the proximal portion of the hub comprises a substantially cylindrical body having an outer surface and at least one protrusion extending from the outer surface at or proximate to the proximal end, the protrusion preventing a conventional lock connector from mating with the hub.

12. Combination of claim 9, wherein the proximal portion of the hub comprises a substantially cylindrical body having an outer surface and an opening at the proximal end and at least one protrusion extending from the outer surface at or proximate to the proximal end opening, the cross sectional dimension of at least the opening and the protrusion forming the non-conventional configuration.

13. Combination of claim 9, wherein the proximal portion of the hub comprises a substantially cylindrical body having an outer surface and two protrusions extending from opposite sides of the outer surface at or proximate to the proximal end, the protrusions preventing a conventional slip fit or lock connector from mating with the hub.

14. Combination of claim 9, wherein the proximal portion comprises a substantially cylindrical body having an outer surface and an opening of a predetermined cross sectional dimension at the proximal end and two protrusions extending from opposite sides of the outer surface of the cylindrical body at or proximate to the proximal end to form the non-conventional configuration that enables the hub to mate only with a fluid conveying device having the special connector with the counterpart configuration complementary to the non-conventional configuration, the special connector having threads to matingly accept the protrusions and a nose cone extension that fittingly mates with the opening to lockingly couple the needle assembly and the fluid conveying device to each other.

15. Combination of claim 9, wherein the proximal portion comprises a substantially cylindrical body having an outer surface and an opening at the proximal end that opens to a through bore in the cylindrical body, wherein the cylindrical body, the opening and the bore have respective cross sectional dimensions that form the non-conventional configuration that prevents the needle hub from fittingly mating with a conventional slip fit connector.

16. Combination of claim 9, wherein the needle comprises an epidural needle.

17. Combination of claim 9, wherein the fluid conveying device comprises a syringe, a fluid bag or a fluid line.

18. Combination of claim 9, wherein the fluid conveying device comprises a lock type syringe and wherein the special connector comprises a circumferential wall circumscribing a special nose cone extension, the wall having special threads formed at its inner circumferential surface and the special nose cone extension having a special dimension, the special threads and special nose cone extension forming the counterpart configuration complementary to the non-conventional configuration.

19. Combination of claim 9, wherein the fluid conveying device comprises a slip fit type syringe and wherein the special connector comprises a special nose cone extension having a special dimension forming the counterpart configuration complementary to the non-conventional configuration.

20. Combination of claim 9, wherein the fluid conveying device comprises a fluid line and wherein the special connector comprises a circumferential wall circumscribing a special nose cone extension, the wall having special threads formed at its inner circumferential surface and the special nose cone extension having a special dimension, the special threads and special nose cone extension forming the counterpart configuration complementary to the non-conventional configuration, the special connector connecting the hub of the needle assembly to the fluid line.

* * * * *